United States Patent [19]

Taguchi et al.

[11] Patent Number: 4,960,903
[45] Date of Patent: Oct. 2, 1990

[54] AROMATIC COMPOUNDS HAVING SULFONYL GROUPS

[75] Inventors: Yoshio Taguchi, Iruma; Chichiro Imai, Yokohama; Yoshio Imai, Oota, all of Japan

[73] Assignee: Toa Nenryo Kogyo Kabushiki Kaisha, Tokyo, Japan

[21] Appl. No.: 939,105

[22] Filed: Dec. 8, 1986

[30] Foreign Application Priority Data

Dec. 16, 1985 [JP] Japan ............... 60-281077
Dec. 16, 1985 [JP] Japan ............... 60-281078

[51] Int. Cl.$^5$ .............. C07D 307/89; C07D 403/10; C07D 149/34; C07D 147/06
[52] U.S. Cl. ..................... 548/461; 568/29; 568/33; 568/34
[58] Field of Search ............ 568/33, 34, 29; 548/455, 461

[56] References Cited

U.S. PATENT DOCUMENTS 3,933,862 1/1976 Williams et al. ............ 549/241
4,102,905 7/1978 Williams et al. ............ 549/241
4,179,461 12/1979 Marhold et al. ............. 568/33

FOREIGN PATENT DOCUMENTS 117416 9/1984 European Pat. Off. .
1950394 4/1970 Fed. Rep. of Germany .
1668029 7/1971 Fed. Rep. of Germany .
2003112 7/1971 Fed. Rep. of Germany .

*Primary Examiner*—David B. Springer
*Attorney, Agent, or Firm*—Wenderoth, Lind & Ponack

[57] ABSTRACT

An aromatic compound having sulfonyl groups, as an intermediate or raw material of polyimides having a good and well-balanced heat resistance and moldability is effectively produced by reacting a compound represented by the general formula, R—Ar—R wherein Ar is

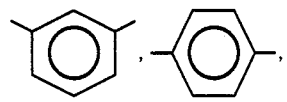

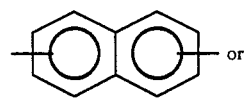

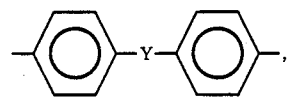

Y is a bond, oxygen atom, sulfur atom, SO$_2$, CH$_2$ or

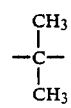

and R is a hydrogen atom or —SO$_2$X and X is a halogen atom or alkali metal, with a compound represented by the following general formula,

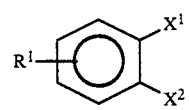

wherein X$^1$ and X$^2$ are simultaneously methyl groups or form

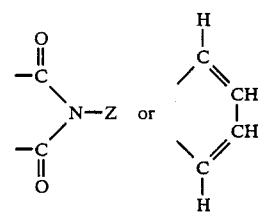

and Z is a hydrogen atom, alkyl group having 1 to 6 carbon atoms or aryl group having 6 to 8 carbon atoms and R$^1$ is a hydrogen atom, —SO$_2$X, halogen atom or nitro group, X is a halogen atom or alkali metal and R and R$^1$ are not same simultaneously, either of which contains —SO$_2$X group as a necessary group.

8 Claims, No Drawings

AROMATIC COMPOUNDS HAVING SULFONYL GROUPS

BACKGROUND OF THE INVENTION

1. Field of the Invention

This invention relates to a novel aromatic compound having sulfonyl groups and a process for the production of the same.

2. Description of the Prior Art

A number of aromatic compounds having functional groups such as carboxyl and imide groups have hitherto been known as raw materials for heat resisting polymers. For example, pyrometallic acid (anhydride) typical of which is Kapton is known as a raw material of polyimide and an aromatic bis(etheric anhydride) is known as a raw material of polyether imide (Japanese Patent Application OPI (Kokai) No. 24242/1975. U.S. Pat. No. 4,102,905 describes an aromatic tetracarboxylic acid anhydride having sulfonyl groups which is useful as an intermediate of polyimide and which production, however, is carried out by oxidizing a sulfide with an oxidizing agent such as potassium bichromate to form its sulfone.

However, the polyimide obtained using pyromellitic acid (anhydride) as a raw material is excellent in heat resistance, but inferior in moldability, and the polyether imide obtained using an aromatic bis(etheric anhydride) as a raw material has a low heat resistance.

Many studies have been made to develop a polyimide excellent in moldability. For example, polyether imides are reported in Japanese Patent Application OPI (Kokai) Nos. 69196/1975 and 69197/1975. However, these polyimides exhibit an improved moldability, but have some problems in the heat resistance as the intrinsic character of polyimide.

SUMMARY OF THE INVENTION

It is anobject of the present invention to provide an aromatic compound having sulfonyl groups, as an intermediate or raw material of polyimides having a good and well-balanced heat resistance and moldability.

It is another object of the present invention to provide a process for the production of an aromatic compound having sulfonyl groups, as an intermediate or raw material of polyimides.

It is a further object of the present invention to provide a polyimide with a balanced heat resistance and moldability.

It is a still further object of the present invention to provide an improved process for the production of a polyimide with a balanced heat resistance and moldability.

These objects can be attained by an aromatic compound having sulfonyl groups, represented by the following general formula,

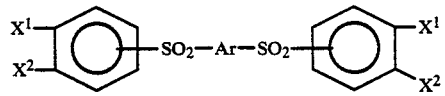

wherein Ar is

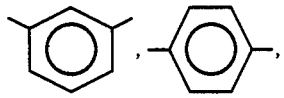

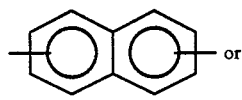

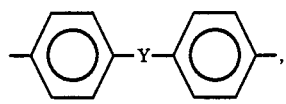

Y is a bond, oxygen atom, sulfur atom, $SO_2$, $CH_2$ or

$X^1$ and $X^2$ are simultaneously methyl groups or form

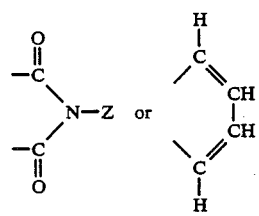

and Z is a hydrogen atom, alkyl group having 1 to 6 carbon atoms or aryl group having 6 to 8 carbon atoms, and a process for the production of an aromatic compound having sulfonyl groups, represented by the following general formula,

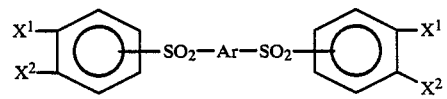

wherein Ar is

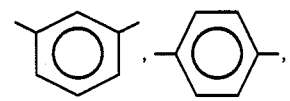

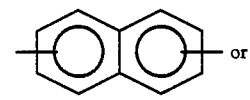

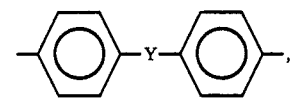

Y is a bond, oxygen atom, sulfur atom, $SO_2$, $CH_2$ or

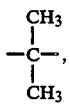

$X^1$ and $X^2$ are simultaneously methyl groups or form

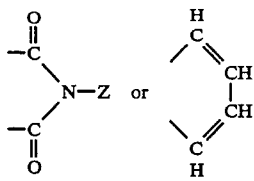

and Z is a hydrogen atom, alkyl group having 1 to 6 carbon atoms or aryl group having 6 to 8 carbon atoms, which process comprises reacting a compound represented by the following general formula,

wherein Ar has the same meaning as described above and R is a hydrogen atom or —$SO_2X$ and X is a halogen atom or alkali metal, with a compound represented by the following general formula,

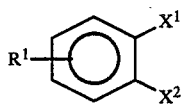

wherein $X^1$ and $X^2$ have the same meaning as described above and $R^1$ is a hydrogen atom, —$SO_2X$, halogen atom or nitro group, X is a halogen atom or alkali metal and R and $R^1$ are not same simultaneously, either of which contains —$SO_2X$ group as a necessary component.

DETAILED DESCRIPTION OF THE INVENTION

The inventors have made various efforts and consequently, have succeeded in producing an aromatic tetracarboxylic acid containing sulfonyl groups or its anhydride or its intermediate as a novel compound in an economical process on a commercial scale. In addition, the inventors have also succeeded in obtaining an aromatic polyimide containing sulfonyl groups from the above described aromatic tetracarboxylic acid.

Accordingly, the present invention provides a process for the production of an aromatic compound having sulfonyl groups, represented by the following general formula,

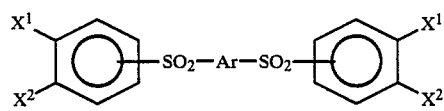
(I)

wherein Ar is

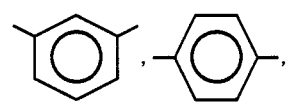

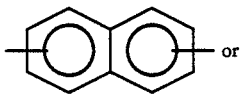

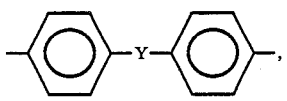

Y is a bond, oxygen atom, sulfur atom, $SO_2$, $CH_2$ or

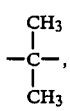

$X^1$ and $X^2$ are simultaneously methyl groups or form

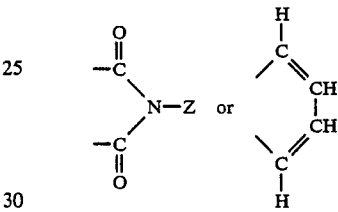

and Z is a hydrogen atom, alkyl group having 1 to 6 carbon atoms or aryl group having 6 to 8 carbon atoms, which process comprises reacting a compound represented by the following general formula,

wherein Ar has the same meaning as described above and R is a hydrogen atom or —$SO_2X$ and X is a halogen atom or alkali metal, with a compound represented by the following general formula,

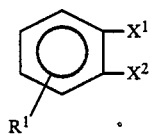

wherein $X^1$ and $X^2$ have the same meaning as described above and $R^1$ is a hydrogen atom, —$SO_2X$, halogen atom or nitro group, X is a halogen atom or alkali metal and R and $R^1$ are not same simultaneously, but either of R and $R^1$ contains —$SO_2X$ as an essential group.

The aromatic compound (I) having sulfonyl groups produced by the above described process is a novel compound useful as an intermediate for producing an aromatic tetracarboxylic acid having sulfonyl groups or its anhydride, and for producing therefrom an aromatic polyimide (II) having sulfonyl groups, which is excellent in well-balanced heat resistance and moldability.

That is, the present invention further provides the aromatic compound (I) having sulfonyl groups, represented by the above described general formula, and the aromatic polyimide (II) having sulfonyl groups, represented by the following recurring unit,

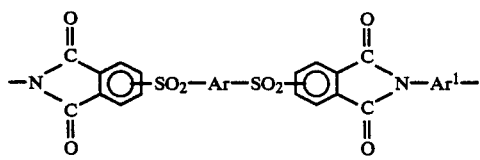

wherein Ar has the same meaning as described above and Ar¹ is

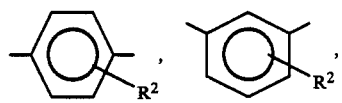

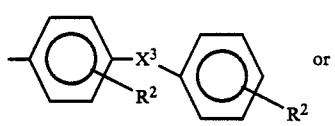

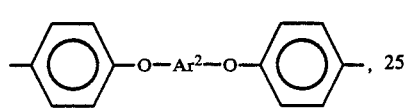

R² being a hydrogen atom or methyl group X³ being a bond, oxygen atom, sulfur atom, SO₂, CH₂ or

and Ar² being

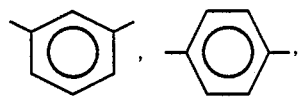

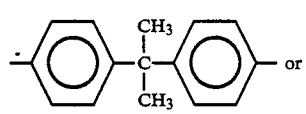

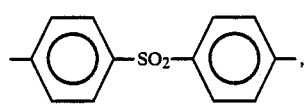

and having an intrinsic viscosity of 0.1 to 10.0 dl/g.

Preferred embodiments of the process according to the present invention will be illustrated:

(1) Production of a compound in which X¹ and X² both are methyl groups in General Formula (I)

(i) A compound (A) represented by the general formula,

X—SO₂—Ar—SO₂—X    (A)

wherein Ar has the same meaning as that of General Formula (I) and X is a halogen atom, is reacted with o-xylene to synthesize a compound (B) represented by the general formula;

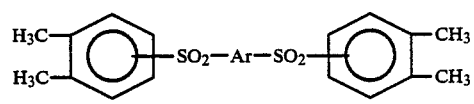

(ii) A compound represented by the formula,

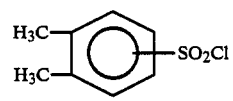

is reacted with a compound represented by the general formula,

R—Ar—R wherein R is a hydrogen atom, to synthesize Compound (B).

(2) Production of a compound in which X¹ and X² form

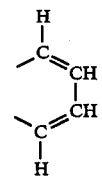

in General Formula (I)

A compound represented by the formula,

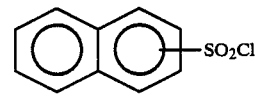

is reacted with a compound represented by the general formula,

R—Ar—R wherein R is a hydrogen atom, to synthesize a compound (C) represented by the general formula,

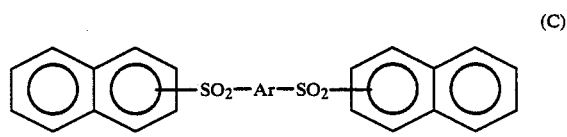

(3) Production of a compound in which X¹ and X² form

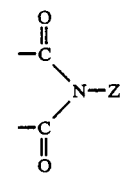

in General Formula (I)

A compound (D) represented by the general formula,

 (D)

wherein Ar has the same meaning as Ar of General Formula (I), is reacted with a compound (E) represented by the general formula,

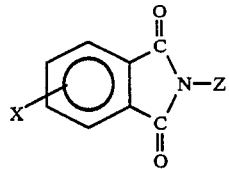 (E)

wherein Z has the same meaning as Z of General Formula (I) and X is a chlorine atom, fluorine atom or nitro group, to synthesize a compound (F) represented by the general formula,

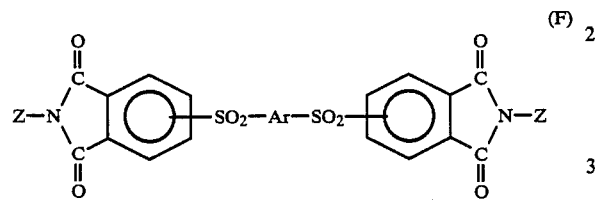 (F)

(4) Production of a compound corresponding to General Formula (I) wherein $X^1$ and $X^2$ both are carboxyl groups (i) Compound (B) obtained in the above described (1) or Compound (C) obtained in the above described (2) is subjected to oxidation to synthesize a compound (G) represented by the general formula,

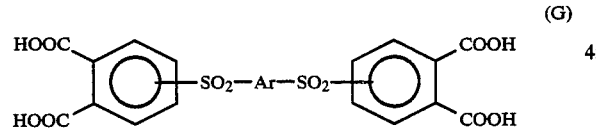 (G)

(ii) Compound (F) obtained in the above described (3) is subjected to hydrolysis to synthesize a compound (G).

(5) Production of a compound corresponding to General Formula (I) wherein $X^1$ and $X^2$ form a linkage of

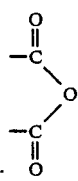

Compound (G) obtained in the above described (4) is subjected to dehydration to synthesize a compound (H) represented by the general formula,

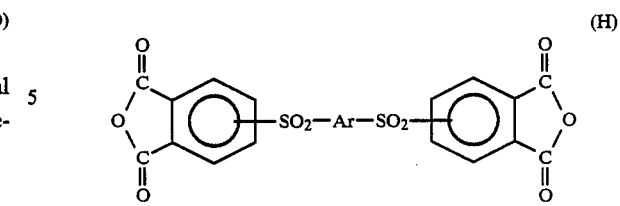 (H)

The above described Processes (1) to (5) will now be illustrated in greater detail:

PROCESS (1)

Case (i)

Compound (B) can be obtained by reacting Compound (A) with o-xylene. Useful examples of Compound (A) represented by the foregoing general formula are m-dichlorosulfonylbenzene, m-dibromosulfonylbenzene, p-dichlorosulfonylbenzene, p-dibromosulfonylbenzene, 1,5-dichlorosulfonylnaphthalene, 1,6-dichlorosulfonylnaphthalene, 2,6-dichlorosulfonylnaphthalene, 2,7-dichlorosulfonylnaphthalene, 1,5-dibromosulfonylnaphthalene, 2,6-dibromosulfonylnaphthalene, p,p'-dichlorosulfonylbiphenyl, p,p'-dichlorosulfonyldiphenyl ether, p,p'-dichlorosulfonyldiphenyl thioether, p,p'-dichlorosulfonyldiphenylsulfonyl, p,p'-dichlorosulfonyldiphenylmethane, p,p'-dichlorosulfonyldiphenyl-i-propylidene, p,p'-dibromosulfonyldiphenyl ether, p,p'-dibromosulfonyldiphenylsulfonyl and the like.

The reaction of Compound (A) and o-xylene is generally carried out by contacting them with agitation at a temperature of $-70°$ C. to $+250°$ C. for 0.5 to 50 hours in the presence of a catalyst, for example, a protonic acid such as sulfuric acid, methanesulfonic acid or trifluoromethanesulfonic acid, a Lewis acid such as aluminum trichloride, boron trifluoride or ferric chloride, or a metallic powder such as iron powder or aluminum powder. The molar proportion of o-xylene to Compound (A) is preferably at least 2, more preferably 2 to 100. The quantity of the catalyst to be used is ordinarily 0.01 to 20 mol per 1 mol of Compound (A).

This reaction can be carried out in the presence of a solvent selected from the group consisting of halogenated hydrocarbons such as methyl chloride, methylene chloride, chloroform, carbon tetrachloride, dichloroethane, trichloroethane, dichloroethylene, trichloroethylene, bromoform, chlorobenzene and dichlorobenzene, nitro compounds such as nitromethane, nitroethane and nitrobenzene, carbon disulfide, and aliphatic or alicyclic hydrocarbons such as, hexane, heptane and cyclohexane.

After the reaction, water is added to the reaction system to decompose the catalyst and the reaction mixture is subjected to steam distillation to distill off the excessive o-xylene, thereby synthesizing Compound (B). The purity of Compound (B) can be raised by recrystallization using an aqueous solution of alcohol.

Case (ii)

Compound (B) can also be synthesized by reacting 3,4-dimethylbenzenesulfonyl chloride or 2,3-dimethylbenzenesulfonyl chloride with H—Ar—H.

Useful examples of H—Ar—H are benzene, naphthalene, biphenyl, phenyl ether, phenyl thioether, diphenylmethane, diphenyl-i-propylidene and the like.

The reaction of dimethylbenzenesulfonyl chloride with H—Ar—H is generally carried out at a temperature of −70° C. to +250° C. for 0.5 to 50 hours in the presence of a solvent such as halogenated hydrocarbons, nitro compounds, carbon disulfide and hydrocarbons which are used in the above described Case (i), and a catalyst such as is used in the above described Case (i). The dimethylbenzenesulfonyl chloride is preferably used in a molar proportion of at least 2, more preferably 2 to 10 to H—Ar—H and the catalyst is preferably used in a proportion of 0.01 to 20 mols to 1 mol of the dimethylbenzenesulfonyl chloride.

After the reaction, water is added to the reaction system to decompose the catalyst and the reaction mixture is subjected to steam distillation or the like to distill off the solvent and unreacted compounds thus obtaining Compound (B).

PROCESS (2)

Compound (C) can be synthesized by reacting α-chlorosulfonylnaphthalene or β-chlorosulfonylnaphthalene with H—Ar—H. This reaction corresponds to that in Case (ii) of the above described Process (1) except that the chlorosulfonylnaphthalene is used instead of the dimethylbenzenesulfonyl chloride and the synthesis can thus be carried out in an analogous manner to Case (ii) of Process (1).

PROCESS (3)

Compound (F) can be synthesized by reacting Compound (D) and Compound (E). Compound (D) corresponds to such a compound that the halogen atom X of Compound (A) represented by X—$SO_2$—Ar—$SO_2$—X is substituted by sodium atom, so examples of Compound (D) are those of Compound (A) in which halogen atoms have been substituted by sodium atoms.

Useful examples of Compound (E) represented by the foregoing formula (E) are 3-chlorophthalimide, 4-chlorophthalimide, N-methyl-3-chlorophthalimide, N-methyl-4-chlorophthalimide, N-ethyl-3-chlorophthalimide, N-ethyl-4-chlorophthalimide, N-n-butyl-3-chlorophthalimide, N-n-butyl-4-chlorophthalimide, N-n-hexyl-3-chlorophthalimide, N-n-hexyl-4-chlorophthalimide, N-phenyl-3-chlorophthalimide, N-phenyl-4-chlorophthalimide, 3-fluorophthalimide, 4-fluorophthalimide, N-methyl-3-fluorophthalimide, N-methyl-4-fluorophthalimide, N-ethyl-3-fluorophthalimide, N-ethyl-4-fluorophthalimide, N-n-butyl-3-fluorophthalimide, N-n-butyl-4-fluorophthalimide, N,N-hexyl-3-fluorophthalimide, N-n-hexyl-4-fluorophthalimide, N-phenyl-3-fluorophthalimide, N-phenyl-4-fluorophthalimide, 3-nitrophthalimide, 4-nitrophthalimide, N-methyl-3-nitrophthalimide, N-methyl-4-nitrophthalimide, N-ethyl-4-nitrophthalimide, N-n-butyl-3-nitrophthalimide, N-n-butyl-4-nitrophthalimide, N-n-hexyl-4-nitrophthalimide, N-phenyl-3-nitrophthalimide, N-phenyl-4-nitrophthalimide and the like.

The reaction of Compound (D) and Compound (E) is generally carried out at a temperature of from room temperature to 200° C. for 1 to 25 hours under anhydrous state in the presence of a solvent. As the solvent, there are preferably used polar solvents such as dimethyl sulfoxide, dimethylformamide, N-methylpyrrolidone, dimethylacetamide, sulfolane and diphenylsulfone. Furthermore, inorganic salts such as potassium carbonate and sodium carbonate can be added to the reaction system.

The ratio of Compound (D) and Compound (E) used in the above described reaction is generally (E)/(D) (mole ratio) of 2 to 5.

After the reaction, the liquid reaction mixture is cooled and poured in water or an alcohol such as methanol, thus obtaining an object, crystal of Compound (F).

PROCESS (4)

Case (i)

Compound (G) can be synthesized by oxidizing Compound (B) or Compound (C). The oxidation reaction of Compound (B) or (C) is generally carried out at a temperature of 100° to 300° C. for 1 to 25 hours in the presence of a solvent, oxidizing agent and aqueous solution of an acid or alkali. As the solvent, there can be used pyridine, acetic acid, acetic anhydride and propionic acid. As the oxidizing agent, there can be used potassium permanganate, potassium bichromate, oxygen and air. As the aqueous solution of an alkali or acid, there can be used aqueous solutions of sodium hydroxide, potassium hydroxide, calcium hydroxide, sulfuric acid and nitric acid.

After the reaction, the reaction mixture is subjected to filtration or distillation to remove solid materials, solvent and water. The thus resulting crystal is dissolved in an aqueous solution of an alkali and then treated with an acid to obtain an object, Compound (G) crystal.

Case (ii)

Compound (G) can also be synthesized by hydrolyzing Compound (F). The hydrolysis of Compound (F) is generally carried out at a temperature of 50° to 200° C. for 1 to 25 hours in the presence of an alkali such as sodium hydroxide or potassium hydroxide, polar solvent such as is described above and water. The alkali is preferably used in a proportion of 0.01 to 20 mols to 1 mol of the imide group in Compound (F).

After the reaction, the reaction mixture is subjected to filtration or distillation to remove solid materials and solvent and then treated with an aqueous solution of an alkali and further with an acid, thus obtaining Compound (G) crystal.

PROCESS (5)

Compound (H) can be synthesized by dehydrating Compound (G). The dehydration reaction of Compound (G) is generally carried out by heating Compound (G) at a temperature of from room temperature to 200° C. for 10 minutes to 25 hours in a dehydrating agent such as acetic anhydride, thionyl chloride or phosphorus pentachloride. Furthermore, Compound (H) can also be obtained by merely heating Compound (G) at a temperature of at least 150° C.

After the reaction, the reaction mixture is cooled or distilled to remove the dehydrating agent, thus obtaining an object, Compound (H) crystal.

The aromatic bissulfone tetracarboxylic acid (or anhydrides) or intermediates thereof according to the present invention are useful as raw materials of polyimides having a well-balanced heat resistance and moldability.

The polysulfone imide of the present invention will hereinafter be referred to as Polyimide (II).

PRODUCTION OF POLYIMIDE (II)

Polyimide (II) can be produced by reacting an aromatic carboxylic acid anhydride, i.e. Compound (H). represented by the following general formula,

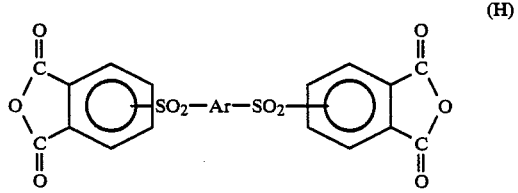

(H)

wherein Ar has the same meaning as Ar in General Formula (I), with an aromatic diamine hereinafter referred to as Compound (J) represented by the following general formula,

$H_2N-Ar^1-NH_2$      (J)

wherein $Ar^1$ has the same meaning as $Ar^1$ in General Formula (II).

Examples of Compound (H) are 4,4'-bis(3,4-dicarboxybenzenesulfonyl)-diphenylether dianhydride, 4,4'-bis(3,4-dicarboxylbenzenesulfonyl)-biphenyl dianhydride, m-bis(3,4-dicarboxybenzenesulfonyl)-benzene dianhydride, 4,4'-bis(2,4-dicarboxybenzenesulfonyl)-diphenylether dianhydride, 4,4'-bis(2,4-dicarboxybenzenesulfonyl)-biphenyl dianhydride and m-bis(2,4-dicarboxybenzenesulfonyl)-benzene dianhydride.

Production of Compound (H) is carried out as described above.

Examples of Compound (J) represented by the above described general formula (J) are m-phenylenediamine, p-phenylenediamine, 2,4-diaminotoluene, 2,6-diaminotoluene, 4,4'-diaminodiphenylmethane, 4,4'-diaminodiphenyl ether, 4,4'-diaminodiphenyl sulfone, 4,4'-diaminodiphenyl sulfide, 2,2'-bis-(p-aminophenyl)-propane, 4,4'-diaminobenzophenone, 4,4'-diaminophenyl, 3,3'-dimethyl-4,4'-diaminobiphenyl, p-bis(4-aminophenoxy)benzene, m-bis(4-aminophenoxy)benzene, bis(4-(4-aminophenoxy)-phenyl)isopropylidene and p,p'-bis(4-aminophenoxy)diphenyl sulfone.

Polyimide (II) is generally synthesized by reacting the above described Compound (H) and Compound (J) at a temperature of at most 50° C. for 10 minutes to 20 hours in the presence of a solvent to form a polyamide carboxylic acid, which is then subjected to dehydration and imide-cyclization.

As the solvent used in the formation of the polyamide carboxylic acid, there are dimethyl sulfoxide, sulfolane, dimethylformamide, dimethylacetamide and N-methylpyrrolidone. The ratio of Compound (H) and Compound (J) used in the above described reaction is preferably (H)/(J) (mole ratio) of 0.9 to 1.1 If necessary, a molecular weight modifier, for example, phthalic anhydride or a monoamine compound such as aniline, ethylamine, propylamine or butylamine can be added in a proportion of up to 10 mol% to 1 mol of Compound (H).

Dehydration and cyclization of a polyamide carboxylic acid can be accomplished by heating a solid or solution of the polyamide carboxylic acid at a temperature of 150° to 400° C. for 1 minute to 5 hours. A solid of a polyamide carboxylic acid is obtained by adding a solution of the polyamide carboxylic acid to a lean solvent such as methanol, ethanol or water to precipitate a polymer which is then dried at a temperature of lower than 50° C.

Moreover, the dehydration and imide-cyclization of a polyamide carboxylic acid can also be carried out by adding a dehydrating agent such as acetic anhydride to a solution or solid of the polyamide carboxylic acid and heating at a temperature of 100° to 200° C., or by heating and then subjecting to azeotropic distillation in a solvent such as toluene, xylene or chlorobenzene. In these cases, a tertiary amine compound such as triethylamine or tributylamine, or pyridine can be added, as a catalyst, in a suitable proportion.

Polyimide (II) can also be produced by adding Compound (H) and Compound (J) to a solvent and reacting them at a temperature of 100° to 250° C. while removing water formed by the reaction. The ratio of Compound (H) and Compound (J) used in the reaction is preferably a (H)/(J) (mole ratio) of 0.9 to 1.1. The molecular weight modifier can also be added. As the solvent, it is preferable to use phenol, o-, m- or p-cresol, or a mixture thereof. The water formed by the reaction can be removed by adding a solvent such as toluene, xylene or chlorobenzene, followed by azeotropic distillation.

The thus produced Polyimide (II) according to the present invention has an intrinsic viscosity of 0.1 to 10.0 dl/g (30° C.).

The polysulfone imide of the present invention is excellent in heat resistance as well as moldability and is thus expected to be used as a raw material for moldings in the fields of space vehicles, aircrafts, electricity, electronics, etc, which need an excellent heat resistance.

The following examples are given in order to illustrate the present invention in greater detail without limiting the same.

Characterization of the compounds of the present invention was carried out using the following instruments and methods:

(i) IR Analysis

Measurement was effected using an infrared spectrophotometer of A-3 type manufactured by Nippon Bunko KK.

(ii) $^1$H-NMR Analysis

Measurement was effected using an NMR spectrometer of Fourier transform type, XL-200 manufactured by Varian Co. (conditions: 200 MHz, 60° C., 98° pulse, pulse interval 5.0 sec., accumulation of 500 transients)

EXAMPLE 1

5 g of p,p'-dichlorosulfonyldiphenyl ether was dissolved in 30 ml of o-xylene and cooled by an ice bath. 6.38 g of anhydrous aluminum chloride was added thereto as solid and stirred at room temperature for 12 hours, to which 100 ml of water was then added to stop the reaction. Then, the excessive o-xylene was removed by steam distillation to obtain 6.7 g of a brown solid. This solid was subjected to recrystallization using a mixed solution of ethanol/water (6:4) to yield a light brown crystal having a melting point of 89° C.

The results of IR Analysis of the resulting crystal are as follows: 1240 $cm^{-1}$ ... —O—; 1315, 1150 $cm^{-1}$ ... —$SO_2$—; 2910-2970 $cm^{-1}$ ... aliphatic CH stretching vibration; 3025-3075 $cm^{-1}$ ... aromatic CH stretching vibration; 1475, 1570 $cm^{-1}$ *l* ... *benzene ring*.

The results of $^1$H-NMR Analysis are as follows: value (ppm) (TMS standard): 2.22 singlet (6H); 2.36 singlet (6H); 7.26–8.30 multiplet (14H).

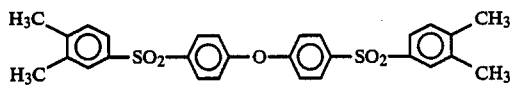

The results of Elementary Analysis are as follows: C=66.78%, H=5.30% (found); C=66.38%, H=5.17% (calculated as $C_{28}H_{26}O_5S_2$).

It is apparent from these results that the material obtained in this example is 4,4'-bis(3,4-dimethylbenzenesulfonyl)diphenyl ether (which will hereinafter be referred to as DXDE) represented by the above described structural formula.

EXAMPLE 2

5 g of 3,4-dimethylbenzenesulfonyl chloride and 1.38 g of diphenyl ether were dissolved in 20 ml of nitrobenzene and cooled by an ice bath. To this solution was added 2.16 g of anhydrous aluminum chloride as solid and stirred at room temperature for 12 hours. 100 ml of water was then added to stop the reaction and the reaction mixture was subjected to steam distillation to remove the nitrobenzene, thus obtaining 3.7 g of a dark solid. The IR spectrum and $^1$H-NMR spectrum of this solid were same as those of the crystal obtained in Example 1. Thus, this solid was DXDE.

EXAMPLE 3

31.9 g of β-chlorosulfonylnaphthalene and 11.9 g of diphenyl ether were dissolved in 100 ml of nitromethane and cooled by an ice bath. To this solution was added 18.76 g of anhydrous aluminum chloride as solid and stirred at room temperature for 12 hours. 300 ml of water was added thereto to stop the reaction and the reaction mixture was then subjected to steam distillation to remove the nitromethane, thus obtaining 39 g of a brown solid having a melting point of 156°–157° C.

The results of IR Analysis of this solid are as follows: 1240 cm$^{-1}$ ... —O—; 1150, 1310 cm$^{-1}$ ... —SO$_2$—; 1480, 1570 cm$^{-1}$ ... aromatic ring.

The results of Elementary Analysis of this solid are as follows: C=73.98%, H=4.09% (found); C=74.12%, H=4.20% (calculated as $C_{32}H_{22}O_5S_2$).

It is apparent from these results that the material obtained in this example is 4,4'-bis(β-naphthalenesulfonyl)diphenyl ether represented by the following structural formula:

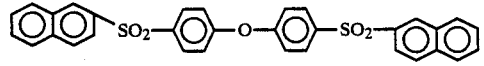

EXAMPLE 4

The procedure of Example 3 was repeated except using α-chlorosulfonylnaphthalene in place of the β-chlorosulfonylnaphthalene used in Example 3 to yield a black solid having a melting point of 109°–110° C.

The results of IR Analysis of this solid are as follows: 1240 cm$^{-1}$ ... —O—; 1308 cm$^{-1}$ ... —SO$_2$—; 1138, 1160 cm$^{-1}$ ... —SO$_2$—; 1480, 1580 cm$^{-1}$ ... aromatic ring.

It is apparent from these results that the thus resulting solid is 4,4'-bis(α-naphthalenesulfonyl)diphenyl ether represented by the following structural formula,

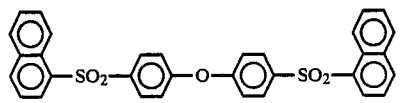

EXAMPLE 5

2 g of DXDE obtained in Example 1 was dissolved in 130 ml of pyridine, to which 0.46 g of potassium hydroxide, 25 g of potassium permanganate and 33 ml of water were added, followed by effecting the reaction with refluxing until the color of potassium permanganate died away. After the reaction, the reaction mixture was cooled, the precipitated solid was separated by filtration and the filtrate was heated to remove the pyridine and water. The precipitated crystal was dissolved in a 10% aqueous solution of sodium hydroxide and acidified with hydrochloric acid to yield 1.8 g of a white crystal. The thus resulting crystal was purified by recrystallization from a mixed solution of methanol/water (6:4). Measurement of the melting point of this crystal was impossible since the dehydration and cyclization reaction took place at 200°–201° C.

The IR spectrum of the purified crystal is as follows: 1245 cm$^{-1}$ ... —O—; 1150, 1320 cm$^{-1}$ ... —SO$_2$—; 1485, 1580 cm$^{-1}$ ... benzene ring; 2200–3600 cm$^{-1}$ ... carboxyl group.

The results of Elementary Analysis of the crystal are as follows: C=53.83%, H=2.99% (found); C=53.68%, H=2.90% (calculated as $C_{28}H_{18}O_{13}S_2$).

It is apparent from these results that the resulting product is 4,4'-bis(3,4-dicarboxybenzenesulfonyl)diphenyl ether (hereinafter referred to as DPDE) represented by the following structural formula,

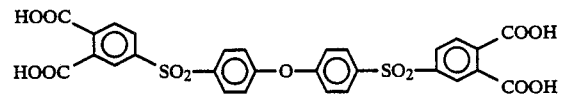

EXAMPLE 6

5 g of N-phenyl-4-nitrophthalimide, 7.84 g of sodium diphenylether-4,4'-disulfinate and 5 g of potassium carbonate were added to 50 ml of dimethyl sulfoxide and reacted at 150° C. for 3 hours in a nitrogen atmosphere. The reaction mixture was cooled and then poured in 1000 ml of methanol to yield 7.64 g of a black and brown solid.

The results of IR analysis of the resulting solid are as follows: 1240 cm$^{-1}$ ... —O—, 1150, 1320 cm$^{-1}$ ... —SO$_2$—; 1480, 1590 cm$^{-1}$ ... benzene ring; 1715, 1770 cm$^{-1}$ ... imide ring.

The results of Elementary Analysis of the solid are as follows: C=65.07%, H=3.02% (found); C=64.86%, H=3.27% (calculated as $C_{40}H_{24}O_9N_2S_2$).

It is apparent from these results that the resulting solid is 4,4'-bis(4-(N-phenylphthalimide)-sulfonyl)-diphenyl ether which will hereinafter be referred to as DPDE-DI, having the following formula:

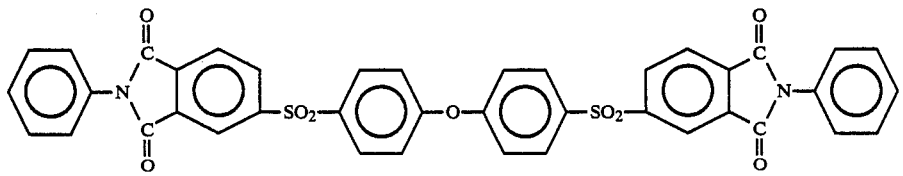

EXAMPLE 7

7 g of DPDE-DI synthesized in Example 6 and 10 g of sodium hydroxide were added to a mixed solution of 10 ml of dimethyl sulfoxide and 10 ml of water and reacted for 8 hours while refluxing. The reaction mixture was poured in 100 ml of a 5% aqueous solution of sodium hydroxide and the solid material was separated by filtration. The filtrate was heated and concentrated, and the precipitated solid was dissolved in 50 ml of a 10% aqueous solution of sodium hydroxide. This solution was acidified with hydrochloric acid to precipitate 3.1 g of a solid.

When this solid was subjected to IR Analysis, the same IR spectrum as that of the crystal obtained in Example 5 was obtained. Thus, the resulting solid was DPDE.

EXAMPLE 8

5 g of DPDE obtained in Example 5 was added to 70 ml of acetic anhydride and reacted for 3 hours with refluxing. When the reaction mixed liquor was cooled, 1.7 g of a white crystal was obtained having a melting point of 276°-277° C.

The results of IR Analysis of this crystal are as follows: 1240 cm$^{-1}$... —O—,; 1150 cm$^{-1}$... —SO$_2$— or acid; 1320 cm$^{-1}$... —SO$_2$—; 1480, 1570 cm$^{-1}$... benzene ring; 1780, 1855 cm$^{-1}$... acid anhydride ring.

The results of Elementary Analysis of the crystal are as follows: C=56.75%, H=2.30% (found); C=56.95%, H=2.39% (calculated as $C_{28}H_{14}O_{11}S_2$).

It is apparent from these results that the resulting crystal is 4,4'-bis(3,4-dicarboxybenzenesulfonyl)-diphenylether dianhydride (hereinafter referred to as DPDE-DA), represented by the following structural formula,

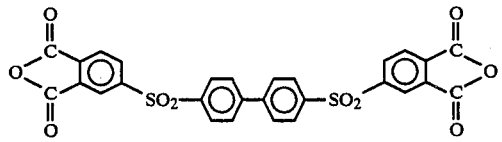

EXAMPLE 9

50 ml of thionyl chloride was added to 5 g of DPDE obtained in Example 5 and reacted for 5 hours with refluxing. After the reaction, the reaction mixture liquor was cooled to yield 2.5 g of a white crystal having a melting point of 272°-273° C. and the same IR spectrum as that of the crystal obtained in Example 8. Thus, this crystal was DPDE-DA.

EXAMPLE 10

To 50 g of p,p'-dichlorosulfonylbiphenyl was added 42 g of anhydrous aluminum chloride, after which 300 ml of o-xylene and 200 ml of nitromethane were added thereto and reacted at room temperature for 20 hours. 500 ml of water was added thereto and heated to remove the excessive o-xylene and nitromethane as a solvent, thus obtaining 47 g of a light cream crystal, which was then recrystallized from 1,2-dichloroethane to yield a crystal having a melting point of 241°-242° C.

The results of IR Analysis of this crystal are as follows: 2910–2970 cm$^{-1}$... aliphatic CH stretching vibration; 3025–3075 cm$^{-1}$... aromatic CH stretching vibration; 1600 cm$^{-1}$... benzene ring, 1320, 1160 cm$^{-1}$... —SO$_2$—.

The results of Elementary Analysis of the crystal are as follows: C=68.70%, H=5.18% (found); C=68.55%, H=5.34% (calculated as $C_{28}H_{26}S_2O_4$).

It is apparent from these results that the resulting crystal is p,p'-bis(3,4-dimethylbenzenesulfonyl)diphenyl represented by the following structural formula,

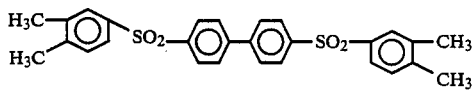

EXAMPLE 11

To 54.8 g of m-benzenedisulfonyl chloride was added 53.1 g of anhydrous aluminum chloride, after which 200 ml of o-xylene and 100 ml of nitromethane were added thereto and reacted for 200 hours at room temperature. 500 ml of water was added thereto and heated to remove the excessive o-xylene and nitromethane as a solvent, thus obtaining 11.4 g of a brown oily material.

The results of IR Analysis of this material are as follows:

2910–2970 cm$^{-1}$... aliphatic CH stretching vibration; 3050 cm$^{-1}$... aromatic CH stretching vibration; 1320 cm$^{-1}$... —SO$_2$—, 1135, 1165 cm$^{-1}$... —SO$_2$—.

The results of Elementary Analysis of this material are as follows: C=63.87%, H=5.25% (found); C=63.74%, H=5.35% (calculated as $C_{22}H_{22}S_2OHD$ 4).

It is apparent from these results that the resulting material is m-bis(3,4-dimethylbenzenesulfonyl)benzene represented by the following structural formula,

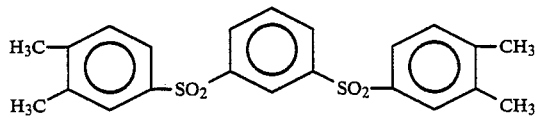

EXAMPLE 12

5 g of 3,4-dimethylbenzenesulfonyl chloride and 1.56 g of naphthalene were dissolved in 20 ml of nitrobenzene and cooled by an ice bath. 2.16 g of anhydrous aluminum chloride as solid was added to this solution and stirred at room temperature for 12 hours, to which 20 ml of water was added to stop the reaction. Then, the nitrobenzene was removed by steam distillation to yield 8.8 g of a yellow solid.

The results of IR Analysis of this solid are as follows: 1150, 1310 cm$^{-1}$ ... —SO$_2$—; 1480, 1570 cm$^{-1}$ ... benzene ring; 1380, 1460 cm$^{-1}$ ... naphthalene ring.

The results of Elementary Analysis are as follows: C=66.52%, H=6.16% (found); C=66.38%, H=6.38% (calculated as C$_{26}$H$_{30}$O$_4$S$_2$).

It is apparent from these results that the material obtained in this example is 2,6-bis(3,4-dimethylbenzenesulfonyl)naphthalene having the formula,

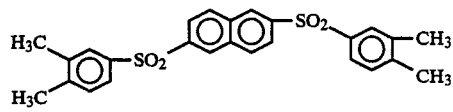

EXAMPLE 13

5 g of 4,4'-dichlorosulfonyldiphenylpropane was dissolved in 30 ml of o-xylene and cooled by an ice bath. To this solution was gradually added 6.25 g of aluminum chloride pulverized and stirred at room temperature for 12 hours, to which 20 ml of water was then added to stop the reaction. The excessive o-xylene was then removed by steam distillation to thus yield 6.8 g of a brown solid.

The results of IR Analysis of the resulting crystal are as follows: 1150, 1315 cm$^{-1}$ ... —SO$_2$—; 2910–2970 cm$^{-1}$ ... aliphatic CH stretching vibration; 3025–3075 cm$^{-1}$ ... aromatic CH stretching vibration; 1190 cm$^{-1}$ ...

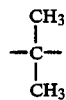

1475, 1570 cm$^{-1}$ ... benzene ring.

The results of Elementary Analysis are as follows: C=70.05%, H=5.88% (found); C=69.92%, H=6.02% (calculated as C$_{31}$H$_{32}$O$_4$S$_2$).

It is apparent from these results that the material obtained in this example is 4,4'-bis(3,4-dimethylbenzenesulfonyl)diphenylpropane represented by the following formula,

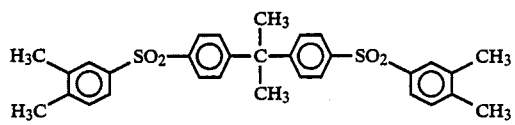

EXAMPLE 14

5 g of 4,4'-dichlorosulfonyldiphenyl ether and 2.22 g of N-methylphthalimide were dissolved in 20 ml of nitrobenzene and cooled by an ice bath. To this solution was gradually added 6.25 g of aluminum chloride pulverized and stirred at room temperature for 12 hours, to which 20 ml of water was then added to stop the reaction. Then, the nitrobenzene was removed by steam distillation to yield 5.2 g of a brown solid.

The results of IR Analysis of the resulting crystal are as follows: 1150, 1320 cm$^{-1}$ ... —SO$_2$—; 1480, 1590 cm$^{-1}$ ... benzene ring; 1715, 1770 cm$^{-1}$ ... imide ring; 2950 cm$^{-1}$ ... —CH$_3$.

The results of Elementary Analysis are as follows: C=58.02%, H=4.69% (found); C=58.44%, H=4.55% (calculated as C$_{30}$H$_{20}$N$_2$O$_9$S$_2$).

It is apparent from these results that the material obtained in this example is 4,4'-bis(4-(N-methylphthalimide)sulfonyl)diphenyl ether represented by the following formula,

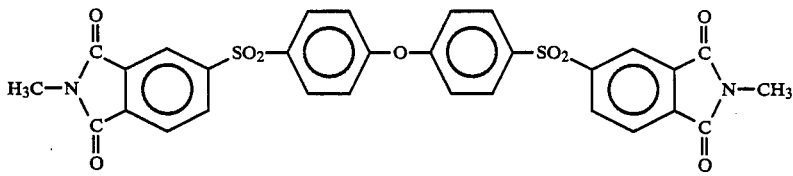

EXAMPLE 15

220.9 mg of 4,4'-diaminodiphenyl ether was dissolved in 3.5 ml of dimethylacetamide, to which 651.5 mg of DPDE-DA obtained in Example 8 was added. The reaction mixture was stirred at room temperature for 3 hours, to which 100 ml of methanol was added to yield 785 mg of a product having an intrinsic viscosity of 0.30 dl/g (30° C., dimethylacetamide).

The results of IR spectrum analysis of this product are as follows: 3700–2400 cm$^{-1}$ ... —COOH; 1720 cm$^{-1}$ ... —COOH; 1640 cm$^{-1}$ ... —CONH—; 1480 cm$^{-1}$ ... benzene ring; 1310 cm$^{-1}$ ... —SO$_2$—, 1230 cm$^{-1}$ ... —O—.

It is apparent from these results that the above described product is a polyamide carboxylic acid having the following recurring unit,

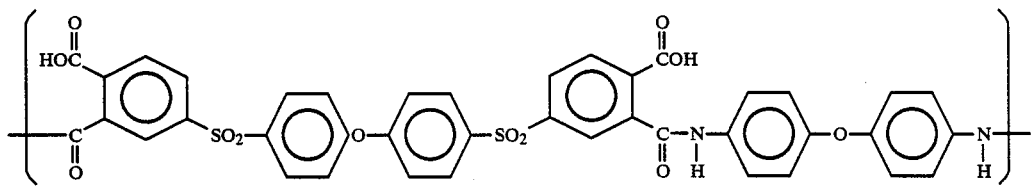

700 mg of the above described product was dissolved in 3 ml of dimethylacetamide, cast on a glass plate, heated at 100° C. for 1 hour to remove the solvent and further heated at 200° C. for 1 hour to obtain a film-shaped product.

IR Analysis of the film-shaped product showed that the absorption of —COOH of 3700–2400 cm⁻¹ disappeared and there was newly found an absorption by imide ring at 1770 and and 1710 cm⁻¹. It is apparent from these results that the film-shaped product is a polysulfone imide having the following recurring unit:

It is apparent from these results that the above described product is a polyamide carboxylic acid having the following recurring unit:

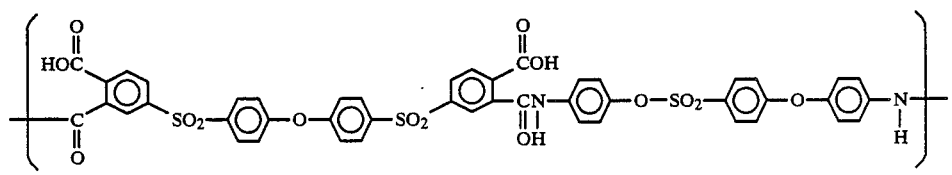

The procedure of Example 15 was repeated except using 700 mg of the above described product to obtain a film-shaped product.

IR Analysis of the thus obtained film-shaped product showed that the absorption by —COOH or 3700–2400 cm⁻¹ disappeared in an analogous manner to Example 15 and there was newly found an absorption by imide ring at 1770 and 1710 cm⁻¹. It is apparent from these results that the film-shaped product is a polysulfone imide having the following recurring unit:

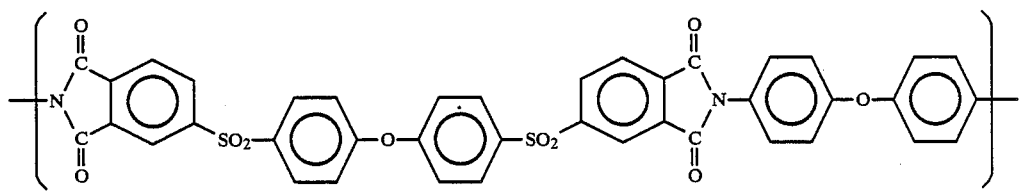

EXAMPLE 16

398.2 mg of p,p'-bis(4-aminophenoxy)-diphenylsulfone was dissolved in 3.7 ml of dimethylacetamide, to which 543.7 mg of DPDE-DA obtained in Example 8 was then added. The reaction mixture was stirred at room temperature for 3 hours and then added to 100 ml of methanol to yield 840 mg of a product having an intrinsic viscosity of 0.27 dl/g (30° C., dimethylacetamide).

The results of IR Analysis of this product are as follows: 3700–2400 cm⁻¹ . . . —COOH; 1720 cm⁻¹ . . . —COOH; 1630 cm⁻¹ . . .

1570, 1480 cm⁻¹ . . . benzene ring; 1300 cm⁻¹ . . . —SO₂; 1210 cm⁻¹ . . . —O—.

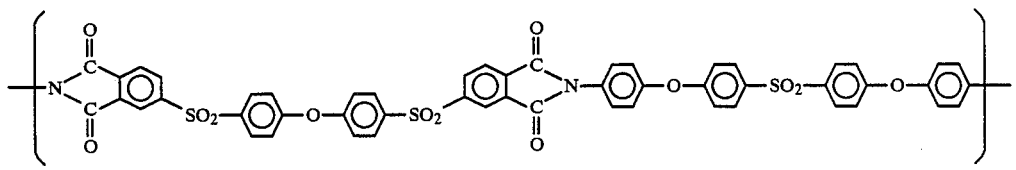

EXAMPLE 17

In an analogous manner to Example 15, DPDE-DA was reacted except using 119.3 mg of m-phenylenediamine in place of the 4,4'-diaminodiphenyl ether as Compound (J) used in Example 15, thus obtaining 730 mg of a product having an intrinsic viscosity of 0.21 dl/g (30° C., diacetamide).

The results of IR Spectrum Analysis of this product are as follows: 3700–2400 cm⁻¹ . . . —COOH, 1720 cm⁻¹ . . . —COOH; 1640 cm⁻¹ . . . —CONH—, 1480 cm⁻¹ . . . benzene ring; 1310 cm⁻¹ . . . —SO₂—, 1230 cm⁻¹ . . . —O—.

It is apparent from these results that the above described product is a polyamide carboxylic acid having the following recurring unit:

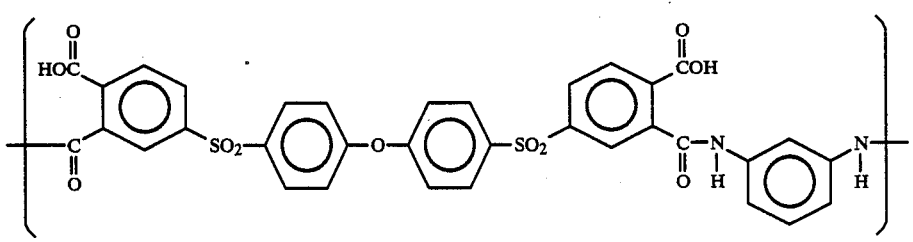

The procedure of Example 15 was repeated except using the above described product to obtain a film-shaped product.

IR Analysis of the film-shaped product showed that the absorption by —COOH of 3700–2400 cm$^{-1}$ disappeared in an analogous manner to Example 15 and there was newly found an absorption by imide ring at 1770 and 1710 cm$^{-1}$. It is apparent from these results that the above described film-shaped product is a polysulfone imide having the following recurring unit:

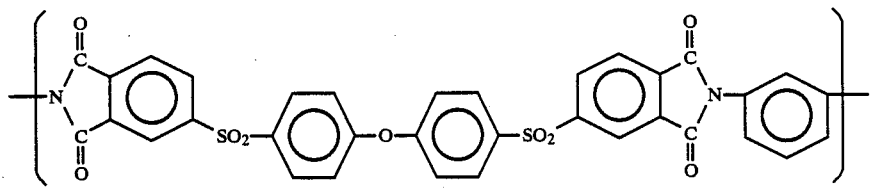

The procedure of Example 15 was repeated except using the above described product to yield a film-shaped product.

IR Analysis of the film-shaped product showed that the absorption by —COOH of 3700–2400 cm$^{-1}$ disappeared in a similar manner to Example 15 and there was newly found an absorption by imide ring at 1770 and 1710 cm$^{-1}$. It is apparent from these results that the above described film-shaped product is a polysulfone imide having the following recurring unit:

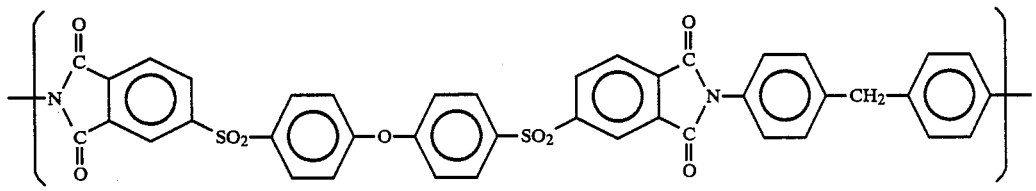

EXAMPLE 18

The procedure of Example 15 was repeated except using 219 mg of 4,4'-diaminodiphenylmethane in place of the 4,4'-diaminodiphenyl ether used in Example 15, thus obtaining a product having an intrinsic viscosity of 0.27 dl/g (30° C., diacetamide).

IR Spectrum of the resulting product is as follows: 3700–2400 cm$^{-1}$ . . . —COOH; 1720 cm$^{-1}$ . . . —COOH; 1640 cm$^{-1}$ . . . —CONH—; 1480 cm$^{-1}$ . . . benzene ring; 1310 cm$^{-1}$ . . . —SO$_2$—.

Therefore, this product is a polyamide carboxylic acid having the following recurring unit:

EXAMPLE 19

The procedure of Example 15 was repeated except using 274 mg of 4,4'-diaminodiphenylsulfone in place of the 4,4'-diaminodiphenyl ether used in Example 15, thus obtaining a product having an intrinsic viscosity of 0.18 dl/g (30° C., diacetamide).

In Spectrum of the resulting product is as follows: 3700–2400 cm$^{-1}$ . . . —COOH; 1720 cm$^{-1}$ . . . —COOH; 1640 cm$^{-1}$ . . . —CONH—, 1480 cm$^{-1}$ . . . benzene ring; 1310 cm$^{-1}$ . . . —SO$_2$—.

Therefore, this product is a polyamide carboxylic acid having the following recurring unit:

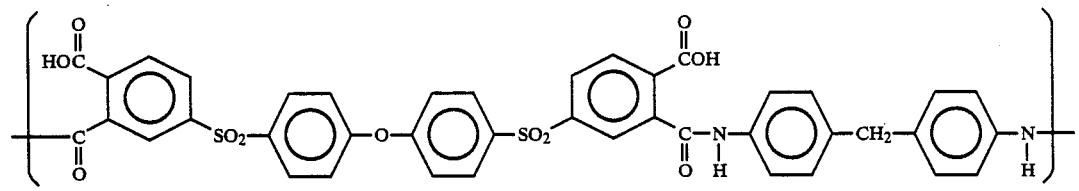

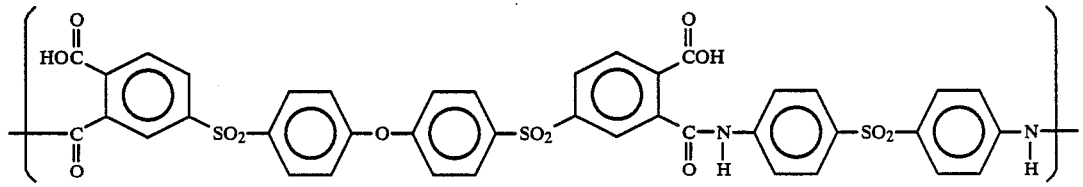

The procedure of Example 15 was repeated except using the above described product to yield a film-shaped product.

IR Analysis of the film-shaped product showed that the absorption by —COOH of 3700–2400 cm$^{-1}$ disappeared in a similar manner to Example 15 and there was newly found an absorption by imide ring at 1770 and 1710 cm$^{-1}$. It is apparent from these results that the above described film-shaped product is a polysulfone imide having the following recurring unit:

The procedure of Example 15 was further repeated except using the above described product to yield a film-shaped product.

IR Analysis of the film-shaped product showed that the absorption by —COOH of 3700–2400 cm$^{-1}$ disappeared in a similar manner to Example 15 and there was newly found an absorption by imide ring at 1770 and 1710 cm$^{-1}$. It is apparent from these results that the above described film-shaped product is a polysulfone imide having the following recurring unit:

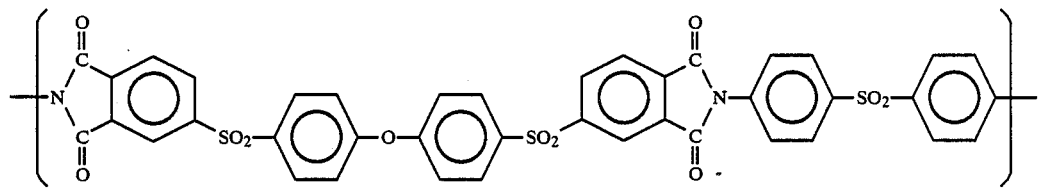

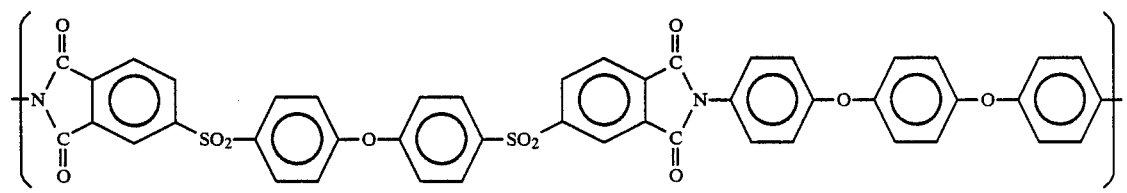

EXAMPLE 20

The procedure of Example 15 was repeated except using 322.5 mg of p-bis(4-aminophenoxy)benzene in place of the 4,4'-diaminodiphenyle ether used in Example 15, thus obtaining a product having an intrinsic viscosity of 0.32 dl/g (30° C., diacetamide).

IR Spectrum of the resulting product is as follows: 3700–2400 cm$^{-1}$ . . . —COOH; 1720 cm$^{-1}$ . . . —COOH; 1640 cm$^{-1}$ . . . —CONH—; 1480 cm$^{-1}$ . . . benzene ring; 1310 cm$^{-1}$ . . . —SO$_2$—.

Therefore, this product is a polyamide carboxylic acid having the following recurring unit:

EXAMPLE 21

The procedure of Example 15 was repeated except using 322.5 mg of m-bis(4-aminophenoxy)benzene in place of the 4,4'-diaminodiphenyl ether used in Example 15, thus obtaining a product having an intrinsic viscosity of 0.27 dl/g (30° C., diacetamide).

IR Spectrum of the resulting product is as follows: 3700–2400 cm$^{-1}$ . . . —COOH; 1720 cm$^{-1}$ . . . —COOH; 1640 cm$^{-1}$ . . . —CONH—; 1480 cm$^{-1}$ . . . benzene ring; 1310 cm$^{-1}$ . . . —SO$_2$—.

Therefore, this product is a polyamide carboxylic acid having the following recurring unit:

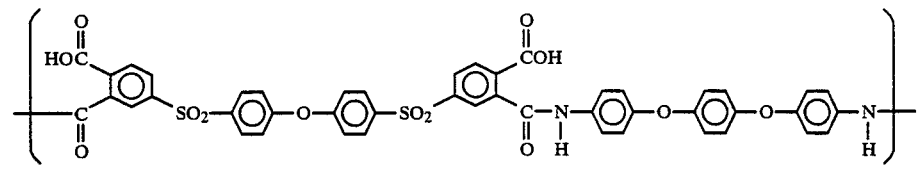

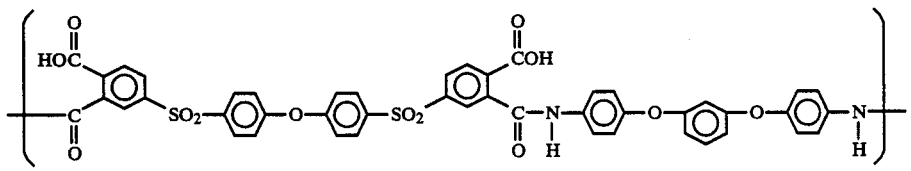

The procedure of Example 15 was repeated except using the above described product to yield a film-shaped product.

IR Analysis of the film-shaped product showed that the absorption by —COOH 3700–2400 cm$^{-1}$ disappeared in a similar manner to Example 15 and there was newly found an absorption by imide ring at 1770 and 1710 cm$^{-1}$. It is apparent from these results that the above described film-shaped product is a polysulfone imide having the following recurring unit:

EXAMPLE 22

The procedure of Example 15 was repeated except using 453 mg of bis(4-(4-aminophenoxy)phenyl)-isopropylidene in place of the 4,4'-diaminodiphenyl ether used in Example 15, thus obtaining a product having an intrinsic viscosity of 0.33 dl/g (30° C., diacetamide).

IR Spectrum of the resulting product is as follows: 3700–2400 cm$^{-1}$ . . . —COOH; 1720 cm$^{-1}$ . . . —COOH; 1640 cm$^{-1}$ . . . —CONH—; 1480 cm$^{-1}$ . . . benzene ring; 1310 cm$^{-1}$ . . . —SO$_2$—.

Therefore, this product is a polyamide carboxylic acid having the following recurring unit:

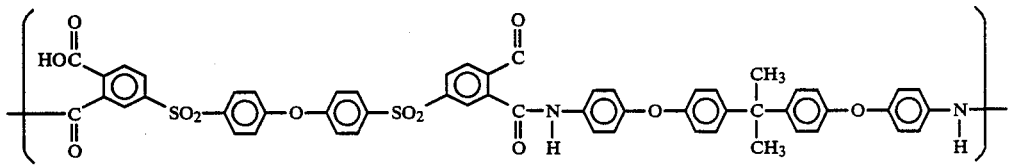

The procedure of Example 15 was further repeated except using the above described product to yield a film-shaped product.

IR Analysis of the film-shaped product showed that the absorption by —COOH of 3700–2400 cm$^{-1}$ disappeared similarly to Example 15 and there was newly found an absorption by imide ring at 1770 and 1710 cm$^{-1}$. It is thus apparent from these results that the

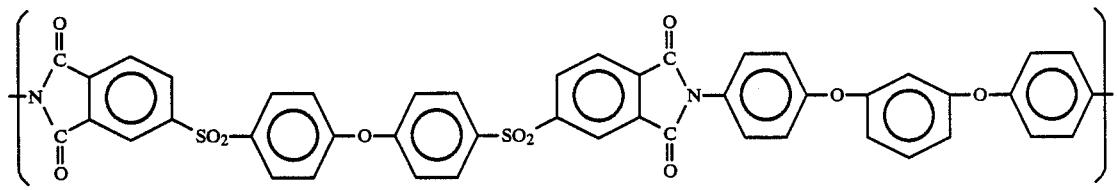

above described film-shaped product is a polysulfone imide having the following recurring unit:

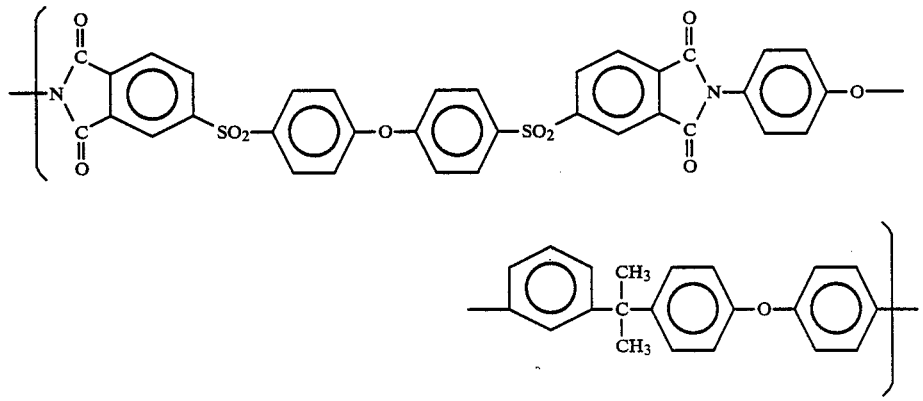

What is claimed is:

1. An aromatic compound having sulfonyl groups, represented by the following formula,

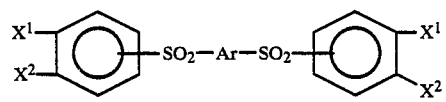

wherein Ar is

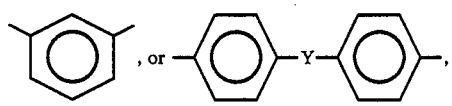

Y is a bond, oxygen atom, sulfur atom, SO₂, CH₂ or

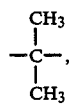

X¹ and X² are simultaneously methyl groups or form

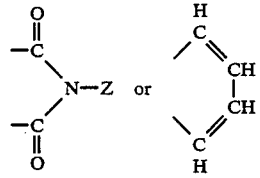

and Z is a hydrogen atom, alkyl group having 1 to 6 carbon atoms or aryl group having 6 to 8 carbon atoms.

2. The aromatic compound having the formula,

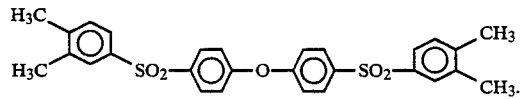

3. The aromatic compound having the formula,

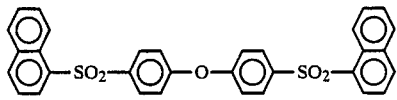

4. The aromatic compound having the formula,

5. The aromatic compound having the formula,

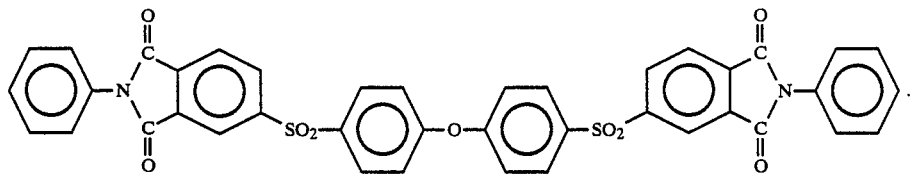

6. The aromatic compound having the formula,

7. The aromatic compound having the formula,

8. An aromatic compound having sulfonyl groups, represented by the following formula:

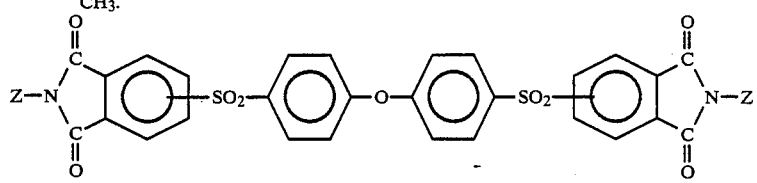

wherein Z is a hydrogen atom, alkyl group having 1 to 6 carbon atoms or aryl group having 6 to 8 carbon atoms.

* * * * *